United States Patent
Mueninghoff

(12)
(10) Patent No.: US 6,387,960 B1
(45) Date of Patent: May 14, 2002

(54) AGRICULTURAL FORMULATIONS CONTAINING MONOGLYCERIDES

(75) Inventor: Jane C. Mueninghoff, The Woodlands, TX (US)

(73) Assignee: Cognis Corporation, Gulph Mills, PA (US)

(*) Notice: Subject to any disclaimer, the term of this patent is extended or adjusted under 35 U.S.C. 154(b) by 0 days.

(21) Appl. No.: 09/185,024

(22) Filed: Nov. 3, 1998

Related U.S. Application Data

(60) Provisional application No. 60/067,422, filed on Dec. 3, 1997.

(51) Int. Cl.⁷ .............................................. A01N 25/30
(52) U.S. Cl. ....................... 514/786; 424/405; 424/406; 504/101
(58) Field of Search ................................ 424/405, 406; 514/786; 504/101

(56) References Cited

U.S. PATENT DOCUMENTS

| | | | | |
|---|---|---|---|---|
| 5,290,751 A | * | 3/1994 | Fiard et al. ................. | 504/116 |
| 5,371,109 A | | 12/1994 | Engstreöm et al. ......... | 514/786 |
| 5,756,128 A | * | 5/1998 | Arimoto ..................... | 424/705 |

FOREIGN PATENT DOCUMENTS

| | | | |
|---|---|---|---|
| JP | 5-271014 | * | 10/1993 |
| WO | 9639846 | * | 12/1996 |

* cited by examiner

*Primary Examiner*—Neil S. Levy
(74) *Attorney, Agent, or Firm*—John E. Drach; Steven J. Trzaska

(57) ABSTRACT

An adjuvant containing: (a) a monoglyceride; and (b) a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof.

6 Claims, No Drawings

AGRICULTURAL FORMULATIONS CONTAINING MONOGLYCERIDES

CROSS-REFERENCE TO RELATED APPLICATIONS

This application claims the benefit of earlier filed and copending provisional application Serial No. 60/067,422, filed on Dec. 3, 1997, the entire contents of which are incorporated herein by reference.

STATEMENT REGARDING FEDERALLY SPONSORED RESEARCH OR DEVELOPMENT

Not Applicable.

BACKGROUND OF THE INVENTION

The present invention generally relates to the use of monoglycerides as emulsifiers, dispersants, wetting agents and solvents for adjuvant concentrates, pesticide concentrates and ready-to-use aqueous pesticide compositions.

Insecticides, insect repellents, fungicides, bactericides, bacteriostats, herbicides, and plant growth regulators are normally formulated into various products for use on crops, for insect control, weed control and the like. Alternatively, the products may be formulated as liquids or powders or granules. Solvents, emulsifiers, dispersing agents and wetting agents are normally incorporated into such compositions to ensure the preparation of a uniform pesticide formulation.

These formulation components are also selected to ensure that the pesticide composition will disperse or emulsify evenly in a tank mix at the point of application. They also have a third purpose which is to ensure optimum delivery of the tank mix preparation to the targeted pest or substrate. Sometimes these surfactants incorporated in pesticide formulations are not sufficient to fully ensure stable tank mixes when such tank mixes contain multiple components. Similarly, it may be necessary to add adjuvants to the tank mix for full stability. It is widely known that adding adjuvants which contain surfactants to the tank mix will realize the desired stabilization. Moreover, additional quantities of surfactants have been shown to potentiate pesticidal activity of many pesticides and there are many adjuvant formulations that have been developed for this purpose. Surfactants are nearly always components of these adjuvants ranging from minor components to the sole component.

BRIEF SUMMARY OF THE INVENTION

The present invention is directed to an adjuvant composition containing:
(a) a monoglyceride; and
(b) a component selected from the group consisting of nonionic surfactants, anionic surfactants, cationic surfactants, alkyl esters, phytobland mineral oils, water soluble silicone surfactants, fatty dialkyl ethers, fatty dialkyl carbonates, vegetable oils, and mixtures thereof.

The present invention is also directed to a pesticide concentrate containing:
(a) an adjuvant containing:
(i) a monoglyceride; and
(ii) a component selected from the group consisting of nonionic surfactants, anionic surfactants, cationic surfactants, alkyl esters, phytobland mineral oils, water soluble silicone surfactants, fatty dialkyl ethers, fatty dialkyl carbonates, vegetable oils, and mixtures thereof; and
(b) a biologically-active ingredient.

The present invention is also directed to a process for treating a target substrate involving contacting the target substrate with the above-disclosed pesticide concentrate.

BRIEF DESCRIPTION OF THE SEVERAL VIEWS OF THE DRAWING

Not Applicable.

DETAILED DESCRIPTION OF THE INVENTION

Other than in the claims and in the operating examples, or where otherwise indicated, all numbers expressing quantities of ingredients or reaction conditions used herein are to be understood as being modified in all instances by the term "about".

The term target substrate as used herein means a plant, a plant pest, or a combination of a plant and a plant pest. A plant pest is defined as any living stage of any weed, insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The monoglycerides of the present invention can provide a variety of functions in agricultural applications. They can serve as wetting agents in dry flowable pesticide formulations, as emulsifiers/co-emulsifiers and dispersing agents in suspoemulsions, microemulsions and aqueous solutions. Monoglycerides are especially useful in combination with nonionic surfactants, and particularly alkyl polyglycosides for imparting both compatability to tank mix formulations and enhanced synergistic surface activity on target substrates.

Monoglycerides are glycerol esters of fatty acid in which only one acid group is attached to the glycerol group. A particularly preferred monoglyceride for use in the present invention is a coconut monoglyceride sulfate.

Suitable co-surfactants/solvents include, but are not limited to, other nonionic surfactants such as ethoxylated castor oils, alcohol ethoxylates, alkyl polyglycosides, glucamides and the like, anionic surfactants such as fatty alcohol ether sulfates, phosphate esters, sulfonates, and the like, cationic surfactants such as ethoxylated fatty amines, and the like, alkyl esters such as methyl oleate, ethyl canolate, and methyl soyate, phytobland mineral oils, water-soluble silicone surfactants, fatty dialkyl ethers, fatty dialkyl carbonates, vegetable oils such as canola oil, soybean oil and the like, and mixtures thereof, typically employed in adjuvant and pesticide compositions.

The co-surfactant/solvent of the present invention will typically be present in the adjuvant composition in an amount of from about 1 to about 99% by weight, preferably from about 10 to about 95% by weight, and most preferably from about 25 to about 90% by weight, based on the weight of the adjuvant composition.

According to another embodiment of the present invention, there is provided a pesticide concentrate containing a mixture of the above-disclosed adjuvant composition and a biologically active ingredient.

Suitable biologically-active ingredients for use in the pesticide concentrates of the present invention are generally selected from the group consisting of insecticides; insect repellents, fungicides, bactericides, bacteriostats, herbicides, and plant growth regulators, all of which are based on biologically-active ingredients. Suitable insecticides include, for example, O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl)thiophosphate, O-ethyl O-p-cyanophenyl-O-phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenyl acetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2H-pyridazine-6-yl)phosphorothioate, O,O-dimethyl S-(1-methyl-2-ethylsulfinyl)-ethyl phosphorothioate, O,O-dimethyl S-phthalimidomethyl phosphorodithioate, O,O-diethyl 2,2,2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin]oxide, 1-(4-chlorophenyl)-3-(2,6-difluorobenzoyl)urea and S-tricyclohexyltin O,O-diisopropylphosphorodithioate; 2-methyl-2-(methylthio) propionaldehyde O-(methylcarbamoyl)oxime; ethyl[2-(4-phenoxyphenoxy)ethyl]carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate; dimethyl N,N'-(thiobis(methylimino)carbonyloxy)-bis(ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2,2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate; 3-phenoxybenzyl-(1-RS)-cis, trans-3-(2,2-dichlorovinyl)-2,2-dimethylcyclopropanedicarboxylate.

Insect repellents which may be employed include but are not limited to 2-ethyl-1,3-hexanediol; N-octyl bicycloheptene dicarboximide; N,N-diethyl-M-toluamide; 2,3:4,5-Bis (2-butylene)tetrahydro-2-furaldehyde; Di-n-propyl isocinchomeronate; and 2-hydroxyethyl-n-octyl sulfide.

Fungicides which may be employed include but are not limited to 3,3'-ethylenebis(tetrahydro-4,6-dimethyl-2H-1,3, 5-thiadiazine-2-thione), zinc or manganese ethylenebis (dithiocarbamate), bis-(dimethyldithiocarbamoyl) disulfide; zinc propylenebis(dithiocarbamate), bis (dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10,11-dehydrodibenzo (b,f)azepine; pyridine fungicides such as zinc bis(1-hydroxy-2(1H) pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene; 1,4-dichloro-2,5-dimethoxybenzene; 5-methyl-s-triazol-(3, 4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiaziazole; 2,4-dichloro-6-(0-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)5-ethenyl 5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D, L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl) thiocarbamate hydrochloride; piomycin; S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may be employed include but are not limited to N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4, 6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis (isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether,2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl) carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate, S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-di-methyl-4,4'-bispyridinium dichloride; phosphoric herbicides such as N-(phosphonomethyl)glycine; aniline herbicides such as alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro-6-trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methyl-phenoxy)pyridazine.

According to another embodiment of the present invention, there is thus provided a pesticide concentrate containing: (a) from about 99.9 to about 5% by weight, preferably from about 95 to about 15% by weight, and most preferably from about 90 to about 20% by weight, of the above-disclosed adjuvant; and (b) from about 0.1 to about 95% by weight, preferably from about 5 to about 85% by weight, and most preferably from about 10 to about 80% by weight, of a biologically active ingredient.

The precise amount of biologically active ingredient contained in the pesticide concentrate will oftentimes depend upon the specific end-use application, i.e., the target substrate to be treated, the area to be treated, etc. Thus, it is within the skill of the applicator to determine the specific amount of biologically active ingredient to be used for a particular application.

In order to formulate the pesticide concentrate into a ready-to-use form, it is typically diluted with water to form an aqueous pesticide composition. The ready-to-use aqueous pesticide composition will typically contain from about 0.1% to about 10% by weight, and preferably from about 0.5 to about 5% by weight, based on the weight of the composition, of the above-disclosed pesticide concentrate, the remainder of which will typically be water.

The precise amount of dilution of the pesticide concentrate necessary to form a ready-to-use aqueous pesticide composition will again depend upon the specific application itself, i.e., the target substrate to be treated, the area to be treated, etc. Thus, it is once again within the skill of the applicator to determine the specific amount of water needed to dilute the pesticide concentrate.

Finally, the present invention also provides for a process for treating a target substrate involving contacting the target substrate with an effective amount of the above-disclosed aqueous pesticide composition.

What is claimed is:

1. A pesticide composition comprising:
   (a) from about 1 to about 99% by weight, based on the weight of the composition, of an adjuvant containing:
      (i) a coconut monoglyceride sulfate; and
      (ii) a component selected from the group consisting of nonionic surfactants, anionic surfactants, cationic surfactants, allyl esters, phytobland mineral oils, water soluble silicone surfactants, fatty acid dialkyl ethers, fatty acid dialkyl carbonates, vegetable oils, and mixtures thereof; and
   (b) a biologically active ingredient used for treating plants and plant pests.

2. The composition of claim 1 wherein the adjuvant is present in the composition in an amount of from about 5 to about 99.9% by weight, based on the weight of the composition.

3. The composition of claim 1 wherein the adjuvant is present in the composition in an amount of from about 20 to about 90% by weight, based on the weight of the composition.

4. A process for treating a target substrate comprising contacting the substrate with a pesticide composition containing:
   (a) from about 1 to about 99% by weight, based on the weight of the composition, of an adjuvant containing:
      (i) a coconut monoglyceride sulfate; and
      (ii) a component selected from the group consisting of nonionic surfactants, anionic surfactants, cationic surfactants, alkyl esters, phytobland mineral oils, water soluble silicone surfactants, fatty acid dialkyl ethers, fatty acid dialkyl carbonates, vegetable oils, and mixtures thereof; and
   (b) a biologically active ingredient used for treating plants and plant pests.

5. The process of claim 4 wherein the adjuvant is present in the composition in an amount of from about 5 to about 99.9% by weight, based on the weight of the composition.

6. The process of claim 4 wherein the adjuvant is present in the composition in an amount of from about 20 to about 90% by weight, based on the weight of the composition.

* * * * *